United States Patent [19]

Young

[11] Patent Number: 5,307,813
[45] Date of Patent: May 3, 1994

[54] IN VIVO IMAGING MICROSCOPIC INTERVAL REGIONS OF A PATIENT'S BODY

[75] Inventor: Ian R. Young, Nr. Marlborough, England

[73] Assignee: Picker International, Inc., Cleveland, Ohio

[21] Appl. No.: 922,235

[22] Filed: Jul. 31, 1992

[30] Foreign Application Priority Data

Aug. 23, 1991 [GB] United Kingdom ............... 9118229

[51] Int. Cl.⁵ ..................... A61B 5/055; A61B 6/00
[52] U.S. Cl. ................. 128/653.4; 128/654; 128/658; 128/665
[58] Field of Search ............. 128/653.1, 654, 655, 128/664, 665, 653.2, 653.4, 656–658

[56] References Cited

U.S. PATENT DOCUMENTS

| 4,916,170 | 4/1990 | Nambu et al. |
| 5,017,359 | 5/1991 | Nicolau et al. |
| 5,092,331 | 3/1992 | Nakamura et al. ............... 128/665 |

FOREIGN PATENT DOCUMENTS 2548838  5/1977  Fed. Rep. of Germany ...... 128/654

*Primary Examiner*—Ruth S. Smith
*Attorney, Agent, or Firm*—Timothy B. Gurin

[57] ABSTRACT

In imaging an internal region of the human body, using optical or NMR techniques, a high resolution image is produced by imaging a layer of material formed on the region of interest which conforms to the surface of the region. The material is preferably a lipid, introduced into the body and positioned adjacent the region of interest using a probe.

15 Claims, 1 Drawing Sheet

IN VIVO IMAGING MICROSCOPIC INTERVAL REGIONS OF A PATIENT'S BODY

BACKGROUND OF THE INVENTION

This invention relates to imaging apparatus and methods and, in particular, to apparatus and methods for in vivo imaging of microscopic internal regions of a patient's body.

In some conventional systems for in vivo imaging of internal tissues, a probe is inserted into a channel, normally a naturally-occurring channel, in the body to collect signals representative of the tissue surface to be imaged, and pass the signals to image processing means.

Where the regions to be imaged are microscopically small e.g. of diameter of no more than 1.5 mms, it is difficult to achieve satisfactory resolution.

For example, when using an optical imaging technique wherein a probe directs light from a laser source onto a region of tissue and detects light reflected back from the region onto the probe, the resolution obtainable is limited by the transparency of the tissue and also by very high levels of scattering of light in the tissue. Due to such scattering the mean optical path length is at least 4.4 times that expected on geometric considerations.

When using magnetic resonance imaging techniques the problem arises that water molecules have a diffusion coefficient of around $3.5 \times 10^{-3}$ m$^2$/s at 37° C. in bulk water and the diffusion coefficient of water molecules in body tissue is likely to be much the same. In imaging systems, the time interval between RF excitation of a region and magnetic resonance data acquisition is of the order of 10 ms. Hence, half of the molecules originally excited in one part of the body tissue will have diffused over a distance of around 8 microns before their signals are acquired. Reducing the time interval between excitation and data acquisition requires wider acquisition bandwidths to be used, thus decreasing the signal to noise ratio, and also makes it necessary for stronger spatially encoding gradients to be used.

The water molecule diffusion coefficient can be reduced by restricting the free diffusion of water, but only by a relatively small factor. Alternatively, localised cooling of tissue may slow down diffusion, but this produces only a minor reduction in diffusion before the water molecules begin to form ice.

SUMMARY OF THE INVENTION

It is n object of the present invention to provide methods and apparatus for in vivo imaging of a microscopic internal region of a body in which the above mentioned problems are alleviated.

According to the present invention, there is provided a method of in vivo imaging of a microscopic internal region of a patient's body comprising forming on a surface of said region a layer of material conforming to said surface and producing an image of said layer.

In one particular method according to the invention, the layer is formed so as to have a local thickness, the profile of which is a replica of said surface.

Preferably the layer is formed by introducing into said body a probe carrying a quantity of said material; positioning the probe adjacent said region; and causing said material to contact the surface of said region and form a layer conforming to the surface of said region.

The material may have a hardness which reduces with increase of temperature and at the internal temperature of said body may have a rigidity such as to conform to said surface, the material being held at a lower temperature during introduction and positioning of the probe.

The image may be produced by optical or NMR imaging techniques.

The material used to form the layer is suitably a lipid.

BRIEF DESCRIPTION OF THE DRAWINGS

Two methods of imaging according to the invention and apparatus for carrying out the methods will now be described by way of example with reference to the accompanying drawings in which.

DESCRIPTION OF THE PREFERRED EMBODIMENT

Figure 1:
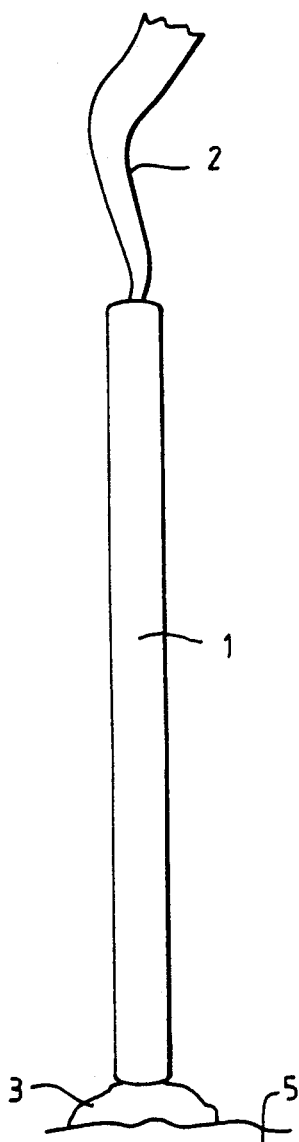
FIG. 1 is a diagram illustrating a probe in position for imaging in one of the methods.

In the first method to be described imaging is effected using an optical technique. The method makes use of a probe 1, as illustrated in FIG. 1, having a cylindrical housing formed from a non-reactive metal such as stainless steel.

Typically, the overall length of the probe 1 is 100 mm, and its diameter, over at least 25 mm of its length, 2.5 mm.

A function of the probe 1 is to carry a quantity of a material to a region of a patient's body to be imaged 5. When the region to be imaged is reached by the probe 1 the material is required to form a layer 3 on the surface of the region to be imaged 5. To this end the material is chosen so as to be fairly stiff at temperatures slightly below the normal temperature of the region of the body being imaged, but to soften to an extend sufficient to take up the shape of the region 5 on being brought into contact with the region 5 and raised to its temperature. In addition the material is required to be biologically compatible with the body containing the region to be imaged. The material is thus suitably a lipid formulated to have the required degree of change of viscosity with temperature.

In addition to carrying the lipid material to the region to be imaged, the probe 1 produces light signals which can be processed to produce an image representation of the region 5. To this end the lipid material carried by the probe 1 includes a small quantity of a fluorescent dye which, in response to incidence thereon of light of one wavelength, emits light of a different wavelength.

The probe 1 carries light guide means 2, e.g. an optical fibre, for directing light of the one wavelength from a laser external to the body containing the region to be imaged 5 onto the layer 3 formed on the region 5, and means for collecting the light consequently emitted by the fluorescent dye in the layer 3 and passing it via the light guide means 2 to image forming means external of the body. The probe 1 further carries a scanning unit (not shown) further described below, which enables the collected light to be capable of use to reconstruct an image.

Before inserting the probe into the body, an amount of the lipid material for forming the layer 3 is placed in a cavity formed at the probe tip using a syringe, a micrometer driven blade being used to remove any excess.

The probe 1 is then introduced into a natural channel in the body until the tip is adjacent the region to be imaged 5. The lipid material is not sufficiently viscous to remain in place on the probe tip whilst the probe 1 is being inserted into the body. The probe 1 therefore carries a cooling system using a Peltier junction (not shown) mounted in silver parts on the probe and inserted in the lipid material to keep the material in position on the probe tip. Once the probe tip is adjacent the region to be imaged 5, the cooling system is switched off and the lipid material is allowed to come to thermal equilibrium with the surrounding body tissue. The lipid material then softens to an extent sufficient for a layer 3 to be formed between the probe 1 and the region to be imaged 5, the layer 3 conforming to the surface of the region to be imaged 5.

When light of the appropriate wavelength is directed onto the layer 3 through a glass window (not shown) at the end of the probe 1, the fluorescent dye molecules in the layer 3 are excited and emit light of a different wavelength which is detected and the resulting signals are processed to produce an image of the layer 3.

Very little scattering of the light produced by the fluorescent dye molecules takes place and therefore imaging of the lipid layer 3 on the region of interest produces a higher resolution image than direct imaging of the region 5 itself.

Figure 2:
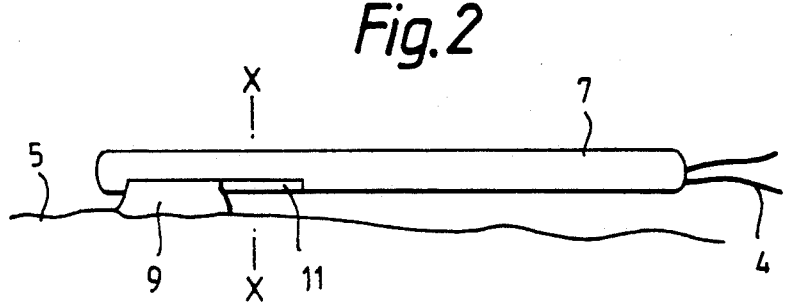
FIG. 2 is a diagram illustrating a probe in the other method.
Figure 3:
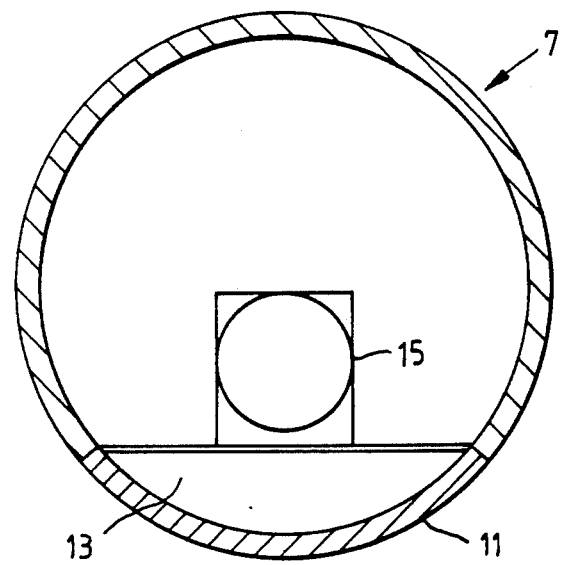
FIG. 3 is an end view of the probe of FIG. 2 along the section line X—X.

In the second method to be described, imaging is effected using a magnetic resonance technique. The method makes use of a generally cylindrical probe 7, as illustrated in FIGS. 2 and 3.

The probe 7 is used to convey a quantity of material from outside the body to the region to be imaged 5. The material is chosen to have biological compatibility and change of viscosity properties with temperature as for the material used in the optical imaging method described above by way of example. In addition the material is chosen to have a diffusion coefficient at the internal temperature of the body which is appreciably less than that of water molecules in the region to be imaged, preferably a diffusion coefficient of less than $5 \times 10^{-5}$ mm$^2$/s. Furthermore the material is required to contain nuclei which can readily be excited to magnetic resonance i.e. hydrogen protons. Thus the material is suitably a lipid as in the optical imaging method described above.

The probe 7 has a compartment 13 within which the lipid material is contained by means of a removable cover 11. A Peltier cooling system (not shown) is used to cool the lipid material until the compartment 13 within the probe 7 is adjacent the region to be imaged 5, after introducing the probe 7 into the body along a natural channel. The cooling system is then switched off, the cover 11 is withdrawn axially and the lipid material contacts the surface of the region to be imaged 5. The warmth of the body tissue softens the lipid so that it forms a layer 9 conforming to the surface of the region 5, the layer having a local thickness, the profile of which is a replica of the surface of region 5.

Magnetic resonance imaging of the layer 9 is then carried out and an image thus obtained which indicates the shape of the region of interest 5. Magnetic resonance signals excited in the layer 9 are detected by coil 15 mounted on the probe 7 adjacent the rear of the compartment 13.

The probe 7 is connected with magnetic resonance imaging apparatus (not shown) via leads 4.

Because the diffusion coefficient of the lipid molecules is considerably less than that of water molecules in the body, the displacement of the hydrogen protons in the lipid during magnetic resonance excitation and detection is negligible. Thus the resolution of the lipid layer image is considerably better than would be the resolution of an image of the region 5 itself.

It will be appreciated that since the lipid resonance frequency is different from that of water, by about 3.5 ppm it is quite possible to image the lipid layer 9 independently of the region of interest 5 itself.

I claim:

1. A method of in vivo imaging of a microscopic internal region of a patient's body comprising:
   forming on a surface of said region a layer of material conforming to said surface, wherein said layer is formed so as to have a local thickness, the profile of said layer being a replica of said surface; and
   producing a image of said layer.

2. A method according to claim 1 wherein said layer is formed by: introducing into said body a probe carrying a quantity of said material; positioning the probe adjacent said region; and causing said material to contact the surface of said region and form a layer conforming to the surface of said region.

3. A method according to claim 2 wherein said material has a viscosity which reduces with increase of temperature and at the internal temperature of said body has a viscosity such as to conform to said surface, the material being held at a lower temperature during introduction and positioning of the probe.

4. A method according to claim 3 wherein during introduction and/or positioning of the probe the material is cooled.

5. A method according to claim 4 wherein the material is cooled using a Peltier junction mounted on the probe.

6. A method according to claim 1 wherein said image is produced by an optical imaging technique.

7. A method according to claim 6 wherein said material includes a component which is fluorescent and said image is produced using light emitted by said fluorescent component.

8. A method according to claim 7 wherein said component, in response to incidence thereon of light of one wavelength, emits light of a different wavelength.

9. A method according to claim 1 wherein said image is produced by a magnetic resonance imaging technique.

10. A method according to claim 9 wherein said material comprises molecules capable of magnetic resonance excitation having a diffusion coefficient at the internal temperature of said body which is appreciably less than that of molecules capable of magnetic resonance excitation in said region.

11. A method according to claim 1 wherein said material is a lipid.

12. An imaging comprising:
    means for introducing a quantity of material into an internal region of a patient's body adjacent a surface of the region to be imaged;
    means for allowing the material to contact the surface and form a layer of material having a local thickness, the profile of said layer being a replica of said surface;
    means for imaging comprising
    means for exciting the formed layer of material to produce image signals;

means for receiving the image signals; and
means for forming an image of the layer from the image signals.

13. The means for imaging comprises as set forth in claim 12 wherein said imaging apparatus is an optical imaging apparatus.

14. The means for imaging comprises as set forth in claim 12 wherein said imaging apparatus is a magnetic resonance imaging apparatus.

15. The apparatus as set forth in claim 12 wherein said introducing means comprises a probe having a cavity for containing said material during introduction of the imaging apparatus into said internal region.

* * * * *